(12) United States Patent
Kitaori et al.

(10) Patent No.: US 7,964,068 B2
(45) Date of Patent: *Jun. 21, 2011

(54) MEMBRANE-ELECTRODE ASSEMBLY, ELECTROLYTIC UNIT USING THE SAME, ELECTROLYTIC WATER EJECTING APPARATUS, AND METHOD OF STERILIZATION

(75) Inventors: Noriyuki Kitaori, Hachioji (JP); Kota Sekido, Sagamihara (JP); Genzo Yamane, Fujisawa (JP); Katsumi Hamaguchi, Fujisawa (JP); Hozumi Tanaka, Fujisawa (JP); Yoshinori Nishiki, Fujisawa (JP); Tsuneto Furuta, Fujisawa (JP)

(73) Assignees: Permelec Electrode Ltd., Kanagawa (JP); Institute of National Colleges of Technology, Japan, Tokyo (JP)

( * ) Notice: Subject to any disclaimer, the term of this patent is extended or adjusted under 35 U.S.C. 154(b) by 810 days.

This patent is subject to a terminal disclaimer.

(21) Appl. No.: 11/858,440

(22) Filed: Sep. 20, 2007

(65) Prior Publication Data

US 2008/0067078 A1 Mar. 20, 2008

(30) Foreign Application Priority Data

Sep. 20, 2006 (JP) .................................. 2006-254874

(51) Int. Cl.
*C25B 9/08* (2006.01)
*C25B 9/10* (2006.01)

(52) U.S. Cl. ........ 204/260; 204/252; 204/283; 204/164; 205/626; 205/629; 205/746; 205/770; 429/479; 429/480; 429/483; 422/186.07; 422/186.18

(58) Field of Classification Search .................. 204/164, 204/252, 260, 283; 429/30, 31, 41, 479, 429/480, 483; 205/629, 626, 746, 770
See application file for complete search history.

(56) References Cited

U.S. PATENT DOCUMENTS

| 5,378,339 A * | 1/1995 | Aoki et al. ..................... 204/260 |
| 2001/0050234 A1 * | 12/2001 | Shiepe .......................... 205/629 |
| 2007/0023273 A1 * | 2/2007 | Kitaori et al. ................. 204/164 |

FOREIGN PATENT DOCUMENTS

| EP | 1741676 A2 | 1/2007 |
| JP | 61-272398 A | 12/1986 |
| JP | 8-134677 A | 5/1996 |
| JP | 9-268395 A | 10/1997 |
| JP | 2000-79393 A | 3/2000 |
| JP | 2000-197889 A | 7/2000 |
| JP | 2001-47048 A | 2/2001 |

(Continued)

OTHER PUBLICATIONS

Chinese Office Action issued in Application No. 200710152217.4, dated Dec. 4, 2009.

(Continued)

*Primary Examiner* — Bruce F Bell
(74) *Attorney, Agent, or Firm* — Sughrue Mion, PLLC (57) ABSTRACT

The present invention provides: a membrane-electrode assembly having a first electrode having a shape of a rod-form or a cylindrical-form, a strip-form diaphragm covering the periphery of the first electrode, and a second electrode disposed on a surface of the strip-form diaphragm; an electrolytic unit containing the membrane-electrode assembly; an electrolytic water ejecting apparatus containing the electrolytic unit; and a method of sterilization using the membrane-electrode assembly.

9 Claims, 6 Drawing Sheets

FOREIGN PATENT DOCUMENTS

| | | |
|---|---|---|
| JP | 2001-253803 A | 9/2001 |
| JP | 2001-276826 A | 10/2001 |
| JP | 2001-342496 A | 12/2001 |
| JP | 2002-145710 A | 5/2002 |
| JP | 2002-346564 A | 12/2002 |
| JP | 2003-93479 A | 4/2003 |
| JP | 2003-266073 A | 9/2003 |
| JP | 2004-129954 A | 4/2004 |
| JP | 2004-130263 A | 4/2004 |
| JP | 2004-130264 A | 4/2004 |
| JP | 2004-130265 A | 4/2004 |
| JP | 2004-130266 A | 4/2004 |
| JP | 2004-148108 A | 5/2004 |
| JP | 2004-148109 A | 5/2004 |
| JP | 2005-029881 A | 2/2005 |
| JP | 2006346203 A | 12/2006 |
| KR | 2006-131687 A | 12/2006 |

OTHER PUBLICATIONS

"The Characteristics of Water and New Application Techniques", pp. 220-222, 2004, NTS Inc.

Extended European Search Report dated Nov. 8, 2005.

Korean Office Action issued on Dec. 31, 2010 in the corresponding Korean Patent Application No. 10-2007-0089128.

* cited by examiner

MEMBRANE-ELECTRODE ASSEMBLY, ELECTROLYTIC UNIT USING THE SAME, ELECTROLYTIC WATER EJECTING APPARATUS, AND METHOD OF STERILIZATION

FIELD OF THE INVENTION

The present invention relates to a membrane-electrode assembly for use in ejecting electrolytic water to be used for sterilization, cleaning, etc., an electrolytic unit structure employing the assembly, an electrolytic water ejecting apparatus (electrolytic water sprayer) employing the structure, and a method of sterilization using these.

BACKGROUND OF THE INVENTION

Bactericide/Disinfectant Solution

Chlorine compound bactericides such as sodium hypochlorite, calcium hypochlorite, and sodium dichloroisocyanurate have been extensively used as bactericides/disinfectants in a wide range of environments. Of these, hypochlorites including sodium hypochlorite are in general use from the standpoints of cost and effect. However, many proposals have been made for attaining improvements in the bactericidal/disinfectant effect thereof which are required in various fields including the clinical field and the food industry (see, for example, JP-A-2001-253803, JP-A-2001-342496, and JP-A-2002-145710.)

Usually, such compositions are prepared by adding the ingredients in water or by mixing aqueous solutions containing the respective ingredients.

Use of Electrolytic Water as Substitute

However, the use of chlorine compound bactericides in large amounts arouses troubles. For example, in factories and retail stores where food materials are handled in large quantities, cleaning with a sodium hypochlorite solution having a concentration exceeding 100 ppm is conducted. This cleaning, however, is regarded as problematic because it not only spoils the flavors of the food materials but also arouses a hazard (increase in THM).

Mainly for the purpose of eliminating those problems, intensive investigations have been made on the usefulness of electrolytic water, i.e., water yielded by electrolysis, in the agricultural, food, clinical, and other fields. The substitution of electrolytic water or ozone-containing water is proceeding mainly in Japan. Electrical energy, which is a clean energy, can be utilized to synthesize hydrogen, oxygen, ozone, hydrogen peroxide, etc. through chemical reactions on electrode surfaces while regulating the reactions. It is known that oxidation reactions especially on the anode yield oxidizing agents effective in water treatments (effective chlorine and peroxides such as ozone) and further generate active species such as OH radicals in some cases (Basic Knowledge of Strongly Acidic Electrolytic Watetr, Ohm-sha, Ltd.).

Attention is being directed to the excellent bactericidal/disinfectant activity of electrolytic water, and investigations are being made on the use of the water in clinical activities and in the home. Examples of the uses thereof which are being investigated include the sterilization/disinfection of diseased parts, incised parts, percutaneous openings for stationary catheters, etc. and the sterilization/disinfection of domestic utensils or articles, such as kitchen utensils, baby articles, and furniture, and house equipments such as the toilet facilities and bathtub. Such electrolytic water is obtained by electrolyzing water (water to be electrolyzed) to which a solute generating ions upon dissolution, e.g., sodium chloride, has been added optionally together with an acid for pH regulation.

Kinds of Electrolytic Water

Besides being used as a food additive, electrolytic water is usable also in other applications. In an electrolytic cell containing water only, the following anode reaction proceeds to evolve oxygen.

$$2H_2O = O_2 + 4H^+ + 4e \quad (1)$$

However, the following reaction proceeds under some catalyst and electrolysis conditions to yield ozone.

$$3H_2O = O_3 + 6H^+ + 6e \quad (2)$$

Thus, ozone-containing water containing the ozone dissolved in the water can be synthesized.

In the case where the water contains hydrochloric acid or chloride ions added thereto, hypochlorous acid is yielded according to formulae (3) and (4).

$$Cl^- = Cl_2 + 2e \quad (3)$$

$$Cl_2 + H_2O = HCl + HClO \quad (4)$$

In the case where the water contains sulfuric acid, the reaction represented by formula (5) proceeds to yield persulfuric acid.

$$2SO_4^{2-} = S_2O_8^{2-} + 2e \quad (5)$$

When carbonate ions are present, the reaction represented by formula (6) proceeds to yield percarbonic acid.

$$2CO_3^{2-} = C_2O_6^{2-} + 2e \quad (6)$$

Through cathode reactions, it is possible to synthesize hydrogenous water, which is water containing excess hydrogen dissolved therein, alkali ion water, and the like.

$$2H^+ 2e = H_2 \quad (7)$$

$$2H_2O + 2e = H_2 + 2OH^- \quad (8)$$

Furthermore, hydrogen peroxide or the like can be synthesized.

As shown above, electrolytic water containing two or more peroxides can be produced with electrolytes suitably selected, besides the acid waters which have been permitted as food additives.

Features of Electrolytic Water (Reference: Characteristics of Water and New Application Techniques, 2004, NTS Inc.)

There are the following three kinds of electrolytic water which have been permitted as food additives.

a) Weakly alkaline electrolytic hypochlorite water (additive name, electrolytic sodium hypochlorite water; 20-200 ppm; pH>7.5; yielded from 0.2-2% aqueous sodium chloride solution using no diaphragm)

b) Slightly acid electrolytic water (additive name, slightly acid hypochlorous acid water; 10-30 ppm; pH=5-6.5; yielded from 2-6% hydrochloric acid using no diaphragm)

c) Strongly acid electrolytic water (additive name, strongly acid hypochlorous acid water; 20-60 ppm; pH<2.7; yielded from 0.2% or lower aqueous sodium chloride solution in diaphragm type cell)

The acid waters among those kinds of electrolytic water have the following and other merits.

(1) The acid waters are superior in safety because THM are less apt to generate under acid conditions.

(2) Resistant bacteria are less apt to generate and on-site management is easy.

(3) The waters can be used for treatment in combination with the alkaline electrolytic water.

(4) The waters can be utilized like tap water and impart no odor to the hands or fingers.

(5) Use of the waters just before suffices (sterilization time is short).

In the conventional treatment with sodium hypochlorite solutions, use of this chemical having a concentration up to 200 ppm as a food additive has been permitted. However, the chemical spoils the flavor and has a residual tendency. In contrast, the electrolytic water of those kinds has a high bactericidal effect even in a low concentration and is beneficial, although use thereof necessitates an initial investment in the apparatus.

Features of Ozone-Containing Water

The long-term use of hypochlorites has yielded bacteria resistant to these chemicals, and there is a doubt about the bactericidal effect thereof On the other hand, ozone-containing water has been placed on food additive lists and has gained approval of FDA (Food and Drug Administrations) of U.S.A. (2001) for use as a bactericide in food storage/production steps. Ozone-containing water has already come into many practical uses for sterilization in food factories and the sterilization of foods themselves. Recently, attention is focused on the fact that ozone-containing water is equal or superior in effect to sterilizing waters heretofore in use also in clinical fields such as dermatology, ophthalmology, and dentistry and is effective in reducing the burden to be imposed on the living body.

Ozone-containing water has the following and other merits.

(1) The bactericidal effect of ozone (OH radicals) is based on the oxidative destruction of cell walls and this indiscriminate activity is thought not to generate resistant bacteria.

(2) Ozone does not have a residual tendency.

When ozone-containing water is used in combination with an oxidizing agent having a residual tendency (e.g., a hypochlorite, persulfate, or percarbonate) according to need, a more effective sterilization treatment is possible.

Conventional Process for Producing Ozone-Containing Water

Ozone-containing water has conventionally been produced generally with a discharge type ozone gas generator. Ozone-containing water having a concentration of several parts per million parts can be easily produced by the process, and is being utilized in the fields of water purification treatment and food cleaning. However, the apparatus has been unsuitable for use as a handy ozone-containing water production apparatus having excellent instant-response characteristics and yielding high-concentration ozone-containing water, for the following reasons.

(1) The ozone-containing water production necessitates two steps, i.e., first generating ozone as a gas and then dissolving the gas in water.

(2) The ozone-containing water has a lower concentration than that produced by the electrolytic process which will be described later and, hence, the water should be produced through high-pressure injection into water and dissolution therein.

(3) The power source for ozone generation has a high voltage and a high frequency, making it difficult to attain a size reduction.

(4) In the ozone-containing water production apparatus based on a discharged, a certain time period (stand-by time of several minutes) is required for the ozone gas generation ability to become stable and it is difficult to instantaneously prepare ozone-containing water having a certain concentration.

Electrolytic Ozone Production Process

The electrolytic process is inferior to the discharge process in electric power consumption rate. However, a feature of the electrolytic process resides in that high-concentration ozone gas and ozone-containing water can be easily obtained. The electrolytic process is hence in general use in special fields such as, e.g., the cleaning of electronic parts. Since a direct-current low-voltage power source is employed because of the principle of the process, the apparatus is excellent in instant-response characteristics and safety and is expected to be used as a small ozone gas generator or a small ozone-containing water production apparatus. According to applications, a driving mode can be selected from battery driving, power-generator driving, and AC-DC conversion driving.

For efficiently generating ozone gas, it is indispensable to select a proper catalyst and electrolyte. Known electrode materials include noble metals such as platinum, α-lead dioxide, β-lead dioxide, glassy carbon impregnated with a fluorocarbon, and diamond. As an electrolyte, use has been made of an aqueous solution containing sulfuric acid, phosphoric acid, fluorinated groups, or the like. However, these electrolytes have poor handleability and are not in extensive use. A water electrolysis cell which employs a solid polymer electrolyte as a diaphragm and in which pure water is used as a raw material is easy to manage in that respect and is in general use [J. Electrochem. Soc., 132, 367 (1985)]. When lead dioxide, which has been employed as a catalyst, is used, ozone gas having a concentration as high as 12% by weight or more is obtained.

In the system called a direct synthesis system, the solution located around an electrode is caused to flow at a sufficient velocity to thereby take out the ozone as ozone-containing water before gasifying (JP-A-8-134677). Furthermore, in the case where raw water other than pure water is supplied to the electrolytic system, the activity of the noble-metal electrode catalyst itself is influenced by the quality of the water. Care should hence be given to the fact that electrolytic performances such as life and efficiency fluctuate. JP-A-9-268395 discloses that conductive diamond is useful as an electrode for producing functional water (containing ozone).

Development of Small Apparatus

Portable small electrolytic water sprayers have been proposed in order to more easily conduct sterilization/disinfection or the like in clinical activities or in the home (see references 1 to 3). Such small apparatus may be extensively used for the deodorization, sterilization, or bleaching of indoor facilities, water-related facilities, tableware, garments, etc. in the home or for business purposes or for the sterilization or disinfection of the human body, e.g., the hands or fingers, etc.

[Reference 1] JP-A-2000-79393
[Reference 2] JP-A-2000-197889
[Reference 3] JP-A-2001-276826

Besides those, the following are known: JP-A-2004-129954 (apparatus having a device which generates power necessary for electrolysis); JP-A-2004-130263 (apparatus in which the proportion of the capacity of the piston to the volume, sectional area, etc. of the cell cylinder part is a specific value); JP-A-2004-130264 (apparatus in which raw water for electrolysis comprising a pH adjustor, surfactant, chlorine compound, and water is used to obtain electrolytic water having a pH of 3-8.5); JP-A-2004-130265 (the electrolytic water according to JP-A-2004-130264 is used in a foamed state); JP-A-2004-130266 (the direction of voltage application to the electrodes is changed alternately); JP-A-2004-148108 (the voltage to be applied to the electrodes is variable); JP-A-2004-148109 (apparatus having electrodes in a suction passage); JP-A-2003-93479, JP-A-2003-266073, and JP-A-2002-346564 (separation type having a cylindrical electrode in a spraying part); and JP-A-2001-47048 (gun type prevented from being clogged during non-spraying period and equipped with a motor).

The electrolytic units in the small electrolytic sprayers proposed so far have had the following problems.

(1) When pure water, well water, or tap water is used as a raw material, the solution has high resistance and, hence, the efficiency of electrolysis is low.

(2) Although an electrolyte is usually added in order to impart conductivity, the electrodes are disposed close to each other in order to reduce the cell voltage. Because of this, the cell structure is complicated.

(3) In some applications, electrolyte addition should be avoided.

(4) Although use of an ion-exchange membrane or the like improves ionic conductivity and this is expected to increase reaction efficiency, it has been difficult to join the membrane or the like with the electrodes.

(5) The membrane usually is nonporous and is used usually in combination with porous electrodes for facilitating the feeding of an electrolytic solution and removal of products. The shapes of the electrodes are hence complicated.

(6) Although particles having an ion-exchange ability may be packed in the space between electrodes, this constitution has many limitations on assembly and structure.

(7) The porous material in a fibrous web form can also be used. However, this material has drawbacks that processing is difficult and availability is poor.

(8) In many ejecting apparatus, the pipings and members are cylindrical and, hence, the electrodes preferably are in a shape suitable therefor, i.e., in the form of a rod or cylinder. There has hence been a desire for an apparatus employing a combination of electrodes having such shape.

It is presumed that if those problems are overcome, the use of electrolytic sprayers expands.

For example, reference 1 discloses, in the FIG. 2 given therein, an embodiment including a platy anode 41 and a platy cathode 42 which are disposed parallel to each other. This embodiment, however, has the following drawbacks. The fixing of the electrodes themselves is difficult. Because this embodiment includes no diaphragm, it is difficult to closely dispose the two electrodes and this tends to necessitate a higher voltage. Furthermore, flow rate regulation is difficult.

SUMMARY OF THE INVENTION

An object of the invention is to provide a membrane-electrode assembly with which many of those problems can be eliminated and which can be easily produced and bring about high performance. Another object of the invention is to provide an electrolytic unit and an electrolytic water ejecting apparatus both employing the assembly and a method of sterilization. The electrolytic water ejecting apparatus of the invention electrolyzes the aqueous solution as a raw material, and the electrolytic water thus yielded can be immediately ejected from the apparatus and used.

The present inventors have made eager investigation to examine the problem. As a result, it has been found that the foregoing objects can be achieved by the following membrane-electrode assembly, electrolytic unit, electrolytic water ejecting apparatus, and method of sterilization with an electrolytic water. With this finding, the present invention is accomplished.

The present invention is mainly directed to the following items:

1. A membrane-electrode assembly comprising: a first electrode having a shape of a rod-form or a cylindrical-form; a strip-form diaphragm covering the periphery of the first electrode; and a second electrode disposed on a surface of the strip-form diaphragm.

2. The membrane-electrode assembly of item 1, wherein the strip-form diaphragm covers the periphery of the first electrode so as to form a space between parts of the diaphragm.

3. The membrane-electrode assembly of item 1 or 2, wherein the strip-form diaphragm spirally covers the periphery of the first electrode.

4. An electrolytic unit comprising: a membrane-electrode assembly comprising: a first electrode having a shape of a rod-form or a cylindrical-form; a strip-form diaphragm covering the periphery of the first electrode; and a second electrode disposed on a surface of the strip-form diaphragm; a tube, the membrane-electrode assembly being fixed in the tube; and an electric supply terminal connected to at least one of the first electrode and the second electrode in the tube.

5. An electrolytic water ejecting apparatus comprising: a vessel containing a raw water; the electrolytic unit according to item 4; a head to eject an electrolytic water prepared by electrolyzing the raw water with the electrolytic unit.

6. A method of sterilization with an electrolytic water, the method comprising: electrolyzing a raw water with a membrane-electrode assembly comprising: a first electrode having a shape of a rod-form or a cylindrical-form; a strip-form diaphragm covering the periphery of the first electrode; and a second electrode disposed on a surface of the strip-form diaphragm to produce a electrolytic water; and ejecting the electrolytic water to a substance to be sterilized.

The invention will be explained below in detail.

The membrane-electrode assembly of the invention comprises a rod-form or cylindrical-form electrode (hereinafter referred to as rod electrode), a strip-form diaphragm covering the periphery of the electrode, and a counter electrode disposed on the surface of the diaphragm. The surface of the diaphram on which the counter electrode is disposed is a back-side surface of a surface facing to the rod electrode. In this membrane-electrode assembly, the rod electrode, diaphragm, and counter electrode have been united together. Because of this, the assembly once produced is easy to handle. This assembly can be produced by a simple operation, e.g., by spirally winding a strip-form diaphragm and a counter electrode around the rod electrode or by covering the rod electrode with a strip-form diaphragm and a counter electrode. The term "spirally" in the invention is a general term for arrangements in which the diaphragm and counter electrode are continuously and obliquely disposed on the periphery of a rod electrode.

In producing this membrane-electrode assembly, the periphery of a rod electrode is covered with a strip-form diaphragm, and a counter electrode is disposed on the surface of the diaphragm. It is preferred that the strip-form diaphragm be disposed so that the periphery of the rod electrode is spirally covered with the diaphragm. In the case of spiral covering, the parts of the strip-form diaphragm which adjoin in the vertical direction may overlap each other. Alternatively, the parts of the strip-form diaphragm which adjoin in the vertical direction may be disposed so as to leave a gap between these. It is desirable that the assembly includes one diaphragm. However, the number of diaphragms is not limited to one, and two or more ring-form diaphragms may be horizontally disposed to cover the periphery of the rod electrode while leaving a gap between these.

Even when an ordinary sheet-form diaphragm is wound around a rod electrode, the covering of the rod electrode with the sheet cannot be smoothly conducted and the resultant membrane-electrode assembly is insufficient in closeness. In contrast, according to the invention, since a strip-form diaphragm is employed and disposed around the rod electrode, a membrane-electrode assembly having high closeness is obtained.

The counter electrode may be a wire-form one and wound around the diaphragm. Alternatively, the counter electrode may be one formed on a surface of the diaphragm by plating, or may be in a foil form and disposed on a diaphragm surface. In the case where a wire-form counter electrode is wound, it is preferred to wind the counter electrode so that it conforms to the shape of the diaphragm. Namely, it is preferred that the counter electrode be wound spirally when the diaphragm is spiral and be wound in a ring arrangement when ring-form diaphragms have been disposed.

This membrane-electrode assembly includes a diaphragm which has been united with the other members. Because of this, by merely incorporating this assembly as it is into any desired electrolytic unit or electrolytic apparatus, the rod electrode and the counter electrode separated therefrom by the diaphragm can be mounted in the electrolytic unit or the like. Furthermore, since the two electrodes are in close contact with each other through the diaphragm, there is no need of dissolving an electrolyte in raw water for electrolysis in order to impart conductivity thereto. In addition, the voltage drop between the two electrodes is almost zero and electrolysis can be conducted at low cost.

This membrane-electrode assembly can be used to constitute an electrolytic unit, which comprises the membrane-electrode assembly, a tube in which the assembly has been fixed, and one or two electric supply terminals connected to the rod electrode and/or the counter electrode in the tube.

In this electrolytic unit, raw water is passed through the tube and brought into contact with the rod electrode and counter electrode to thereby produce any of ozone-containing water, acid water, alkaline water, and the like (hereinafter referred to as electrolytic water). The electrolytic water thus produced is usable in various applications; the suitable concentration of ozone, radicals, etc. varies with applications. The concentration of ozone, etc. depends on the amount of the raw water flowing through the tube per unit time. Consequently, by regulating the diameter of the rod electrode in the tube, the area of the section through which the raw water flows can be regulated. Thus, electrolytic water having a concentration suitable for each of various applications can be produced.

When this electrolytic unit is mounted in an electrolytic water ejecting apparatus comprising a vessel containing raw water stored therein and a head and the raw water is sucked up and passed through the tube, then the raw water comes into contact with the rod electrode and counter electrode in the electrolytic unit and is electrolyzed. As a result, an active species such as ozone is efficiently synthesized in a high concentration to yield electrolytic water having a sterilizing/bleaching ability. This electrolytic water is discharged outside in an atomized or liquid state through the nozzle of the head optionally with a power assist such as, e.g., a pump.

The method of the invention and the electrolytic water ejecting apparatus of the invention can be extensively used for the deodorization, sterilization, or bleaching of indoor facilities, water-related facilities, tableware, garments, etc. in the home or for business purposes or for the sterilization or disinfection of the human body, e.g., the hands or fingers, etc. An apparent from the explanations given above, the term "sterilization" in the method of sterilization of the invention means any of acts such as deodorization, bleaching, and disinfection, besides sterilization.

In the invention, highly active electrolytic water such as the following can be yielded by regulating conditions.

(1) Alkaline electrolytic water (electrolytic water containing two or more peroxides depending on electrolyte selection; sulfates, carbonates, etc., besides chlorides)

(2) Acid electrolytic water (electrolytic water containing two or more peroxides depending on electrolyte selection; sulfates, carbonates, etc., besides chlorides)

(3) High-concentration ozone-containing water (having no residual tendency, having sterilizing activity at least 10 times the sterilizing activity of hypochlorous acid systems, and further having bleaching effect; the ozone half-value period is prolonged depending on coexistent substances, resulting in improved effect retention)

(4) Novel composite electrolytic water (novel sterilizing effect is produced by adding an organic acid/surfactant for pH adjustment for the purpose of improving sterilizing ability or by adding an alcohol or the like for the purpose of, e.g., improving sterilizing ability or refreshing feeling)

The membrane-electrode assembly of the invention, which comprises a rod electrode, a strip-form diaphragm covering the periphery of the electrode, and a counter electrode disposed on the surface of the diaphragm, is an assembly in which the diaphragm has been united with the two electrodes. This assembly therefore is easy to handle and can be easily mounted in various electrolytic water production apparatus.

When the assembly is to be mounted in a tube, the concentration of an electrolytically yielded species in the electrolytic water to be obtained can be regulated to a desired value by regulating the diameter of the rod electrode.

By ejecting or spraying the resultant electrolytic water to or over a substance to be treated, the substance can be sterilized with the electrolytically yielded species contained in the desired concentration.

The reference numerals used in the drawings denote the followings, respectively.

1 electrolytic water sprayer
2 raw water
3 vessel
4 head
5 suction tube
6 electrolytic unit
7 anode (rod electrode)
8 diaphragm
9 cathode (counter electrode)
12 spray nozzle
13 trigger arm
17 trigger-engaged switch

DETAILED DESCRIPTION OF THE INVENTION

The constituent elements of the invention will be explained below. However, the invention should not be construed as being limited to the following.

Anode Material

Either the rod electrode or the counter electrode in the invention may be an anode. In general, however, the rod electrode is an anode and the counter electrode is a cathode.

Examples of anode catalysts for oxidation include lead oxide, tin oxide, noble metals such as platinum, DSAs (electrodes consisting mainly of a noble-metal oxide), carbon, and conductive diamond. From the standpoint of corrosion resistance, it is desirable to use as the electrode catalyst a noble metal such as platinum or iridium, an oxide of such a noble metal, or conductive diamond. The material to be used as an electrode base should have corrosion resistance from the standpoints of attaining a long life and preventing the surface to be treated from being fouled. It is desirable to use as the anode base a valve metal such as titanium or niobium or an alloy thereof. The anode material can be deposited on the surface of such a base having any desired shape heretofore in general use, such as a mesh, pipe, rod, or beads.

The presence of a catalyst as part of the anode suffices, and the base may be partly exposed.

Diamond is regarded as a promising electrode material partly because the electrical conductivity thereof can be regulated by doping. Diamond electrodes are inert in water decomposition reaction. It has been reported that a diamond electrode in oxidation reactions yields ozone and hydrogen peroxide besides oxygen. When conductive diamond is used, electrolysis reactions proceed more readily and those peroxides as products of electrolysis are produced exceedingly efficiently. Furthermore, on the diamond electrode, OH radicals and oxidized forms of electrolytes are yielded besides the electrolytically yielded species shown above. Consequently, the sterilizing/bleaching effects of the OH radicals or oxidized forms and of the electrolytically yielded species can be synergistically utilized.

In the case where conductive diamond is used, examples of usable bases include Nb, Ta, Zr, Ti, Mo, W, graphite, and various carbides as well as Si (monocrystalline and polycrystalline). A suitable one can be selected according to applications.

Cathode Material

Cathode reactions include hydrogen evolution as the main reaction. It is therefore preferred to use an electrode catalyst which is not embrittled by hydrogen. Examples of such preferred electrode catalysts include platinum group metals, nickel, stainless steel, titanium, zirconium, gold, silver, carbon, and diamond. As the cathode base, it is desirable to use stainless steel, zirconium, carbon, nickel, titanium, or the like. In many cases, the electrodes in the apparatus of the invention are disposed so as to come into contact with water containing ozone or a peroxide. It is therefore preferred to employ materials having excellent oxidation resistance.

Diaphragm Material

In order that the active substances generated by electrode reactions might be kept stable, a neutral diaphragm or an ion-exchange membrane can be utilized. The diaphragm may be either of a fluororesin membrane and a hydrocarbon membrane. However, the former membrane is preferred from the standpoint of resistance to corrosion by ozone and peroxides. The ion-exchange membrane not only serves to prevent the substances generated at the anode or cathode from being consumed at the opposed electrode, but also functions to enable the electrolysis to proceed speedily even when the liquid has a low conductivity. Use of an ion-exchange membrane is hence preferred when a raw material having poor conductivity, such as, e.g., pure water, is used.

To make the surfaces of the diaphragm have recesses and protrusions or to form openings in the electrode surfaces is preferred because it can enhance gas/liquid permeability.

Membrane-Electrode Assembly

The length and diameter of the rod electrode in the membrane-electrode assembly are selected according to the desired amount of water to be ejected by spraying and the capacity of the tank. Usually, the length thereof is preferably 10-300 mm and the diameter thereof is preferably 0.5-10 mm. The rod electrode desirably is one having a sectional shape selected from circle, square, ellipse, and the like or one which is in the form of a hollow cylinder or prism. However, the shape of the electrode is not limited to these.

To make the surface of the rod electrode have recesses and protrusions or to form openings in the electrode surface is effective in enhancing gas/liquid permeability. In the case of a hollow material, to form openings in the electrode surface is effective in enhancing gas/liquid permeability.

For securing a water flow, it is preferred to wind the diaphragm around the rod electrode so as to leave a gap between adjoining parts of the diaphragm. The diaphragm may be wound so as to leave no gap.

The strip-form diaphragm preferably has a thickness in the range of 0.1-2 mm and a width in the range of 0.2-20 mm. In case where the width of the diaphragm is smaller than the lower limit, this diaphragm is apt to break in a winding operation because the physical strength thereof is insufficient. In case where the diaphragm is too wide, the movement of the raw material for electrolysis and products of electrolysis through the gap is inhibited, leading to an increase in voltage and a decrease in current efficiency. The width of the gap is preferably about 0.1-10 mm.

It is also preferred to form openings in the strip-form diaphragm beforehand to enhance the gas-liquid permeability of the assembly. The size of each opening is preferably 1-10 mm in terms of the length of the periphery of the opening.

The assembly may have a structure which comprises two or more ring-form strip diaphragms put on the rod electrode and the counter electrode wound around each diaphragm.

In the case where the diaphragm is spirally wound, the angle of winding is governed by the diameter of the rod electrode, width of the diaphragm, and diaphragm gap. For example, when the width of the diaphragm, diaphragm gap, and diameter of the rod electrode are 2 mm, 0.5 mm, and 2 mm, respectively, then the angle is about 20 degrees. As stated above, ring-form diaphragms may be disposed horizontally (angle, 0 degree) so as to leave a gap therebetween.

It is preferred that the end parts of the rod electrode which correspond to the part where the diaphragm and the wire electrode begin to be wound should be cut beforehand to a smaller thickness so as to secure a space for bonding to feeder lines. This is because this cutting enables the assembly part connected to feeder lines to be housed in the suction-passage tube.

The counter electrode preferably is a wire electrode. It is preferred that the counter electrode should have a smaller width than the diaphragm so as not to come into contact with the rod electrode. Besides being in a wire form, the counter electrode may be a foil or a metal gauze cut into a small width. In either case, the counter electrode is disposed on the diaphragm. Alternatively, the counter electrode may be one formed on the surface of the diaphragm by plating, as stated above.

Use may be made of a method in which a catalyst layer is formed on one side of a diaphragm and this diaphragm is wound around the rod electrode so that the side having the catalyst layer faces outward. This method is preferred because the catalyst layer serves as a cathode to facilitate assembly and because the resultant electrolytic unit can have an even current distribution and attain a reduction in cell voltage.

For forming the catalyst layer, an existing method can be used, such as, e.g., electroless plating or PVD. In this constitution also, there are cases where it is preferred to wind a metal wire for the purpose of improving joining with the rod electrode.

Electrolytic Unit

The membrane-electrode assembly is fixed in a tube capable of being connected to a tube-form raw water suction passage to thereby constitute an electrolytic unit. However, the tube may be disposed so as to surround only part of the membrane-electrode assembly. The tube has a diameter sufficient to enable the assembly to be housed therein. However, too large a thickness results in a reduced flow velocity in the tube. In the case of synthesizing ozone-containing water, for example, the decrease in flow velocity reduces the efficiency of gas-liquid contact and is hence unsuitable for obtaining electrolytic water having a high concentration. It is therefore preferred to select the diameter of the tube so as to give electrolytic water having a desired concentration. Concentration regulation may be conducted not by selecting the tube diameter but by selecting the diameter of the rod electrode.

In case where the assembly is not disposed in a tube, most of the electrolytic water yielded cannot be sent to the spraying passage, resulting in a reduced yield of electrolytic water and a reduced concentration.

The material of the tube preferably is a hydrocarbon resin such as PP, PVC, or PE, a fluororesin, a metal, or the like. A tube having heat shrinkability is preferred because the capacity of the electrolytic-unit part can be regulated. The wall thickness of the tube is preferably smaller from the standpoint of rapidly removing the heat generated in the electrolytic unit. However, the wall thickness thereof is preferably from 0.05 mm to 2 mm because mechanical strength also is necessary.

In the sprayer structure which will be described later, the water which is ejected first is the raw water which has not been sufficiently electrolyzed. In view of this, the amount of the water present in the electrolytic unit and the capacity of the other parts of the piping preferably are smaller. However, too thin a piping results in a possibility that water cannot be sucked in a sufficient amount.

Examples of members having appropriate dimensions include a rod electrode having a length of 100 mm and an outer diameter of 2 mm, a diaphragm having a width of 2 mm, gap of 0.5 mm, and thickness of 0.35 mm, and a wire electrode (counter electrode) having a diameter of 0.4 mm. In this case, when a tube having an inner diameter of 5 mm is used, the total number of laps to be made is about 24 and the volume of the space is about 0.9 mL. Consequently, when the sprayer is one in which the amount of water ejected by one operation is 1 mL, fresh electrolytic water can be utilized after about one operation for preliminary ejection (trigger operation).

The two feeder lines extending respectively from the electrodes preferably are covered with an insulating material so as to prevent the lines from coming into contact with each other. It is preferred that the feeder lines which have been led out of the tube should be covered externally with a covering tube having heat shrinkability, fusion-bonded thereto, and separated from the electrolytic water passage in the unit.

In the case of synthesizing ozone-containing water, too short lengths of the piping extending from the electrolytic unit to the spray nozzle are undesirable because the raw water in which the ozone has not sufficiently dissolved is ejected in this case. The more the time period of gas/liquid contact is prolonged, the more the dissolution of the gas-state ozone in the raw water proceeds and the more the efficiency of the synthesis thereof can be heightened. Because of this, it is preferred that the optimal length of that piping be regulated so as to result in a contact time in the range of from 0.1 to 10 seconds.

Raw Water Vessel

The material of the vessel for storing raw water therein is selected from ones which are not attacked by the raw water. The material may be a PE resin when there is no particular problem.

Raw Water and Electrolytic Water Produced

In the case where tap water, well water, or the like is used as raw water, the resistance loss in the cell voltage is not negligible because such water has a low conductivity. It is therefore preferred to heighten the conductivity by dissolving a salt such as $Na_2SO_4$, $K_2SO_4$, NaCl, KCl, or $Na_2CO_3$ as an electrolyte. These salts yield a peroxide upon electrolysis and thereby serve to impart the persistence of a sterilizing effect. The concentration thereof is preferably in the range of 0.01-

10 g/L. When an ion-exchange membrane is used as the diaphragm, there are cases where salt dissolution is unnecessary.

When raw water containing metal ions in a large amount, such as tap water, well water, or seawater, is used, there is a possibility that hydroxides or carbonates might deposit on the surface of the cathode to inhibit reactions. Furthermore, oxides such as silica deposit on the anode surface. For eliminating this problem, a reverse current is caused to flow at an appropriate time interval (from 1 minute to 1 hour), whereby acidification and alkalifying occur at the cathode and the anode, respectively. As a result, reactions for removing the deposits readily proceed while being accelerated by gas evolution and the flow of the raw water.

The composition and concentration of the electrolytic water to be produced can be regulated according to the intended use. In the case where the electrolytic water is intended to be used for food treatment, it should be produced as alkaline electrolytic hypochlorite water, slightly acid electrolytic water, or ozone-containing water. In the case where the electrolytic water is intended to be used for sterilization/bleaching, a peroxide may be suitably selected according to the substance to be treated. In the case of hypochlorous acid, the concentration thereof may be 1-100 ppm. Ozone-containing water may have a concentration of 1-20 ppm. The concentrations of persulfuric acid and percarbonic acid may be 1-100 ppm and 1-100 ppm, respectively.

In the case where hypochlorous acid is to be electrolytically yielded, electrolysis of an acid solution yields hypochlorous acid in a larger amount than a hypochlorite, while use of an alkaline solution yields a hypochlorite in a larger amount than hypochlorous acid. Bactericidal activity varies depending on the nature of the solution. In general, acid solutions often have higher bactericidal activity than alkaline solutions. In the control of, in particular, spores and the like, acid solutions have higher bactericidal activity than alkaline solutions. In contrast, with respect to bactericidal activity against mold, alkaline solutions are more active than acid solutions. It is therefore preferred that the nature of the solution should be suitably regulated so as to be acid or alkaline according to the substance to be treated through ejection to thereby impart improved bactericidal activity thereto.

In case where the solution is acidified by adding a strong acid to the solution to excessively enhance acidity, the hypochlorous acid decomposes to generate chlorine gas and, as a result, the oxidizing ability which brings about the bactericidal activity of hypochlorous acid is impaired. For enhancing the bactericidal activity while maintaining the oxidizing ability of the hypochlorous acid, it is preferred to regulate the solution so as to have a pH of 3-7 at 20° C. For regulating the solution so as to have such a pH, it is preferred to use a water-soluble organic weak acid having a low degree of dissociation from the standpoint of ease of pH adjustment of the solution. Examples of the water-soluble organic acid include succinic acid, lactic acid, acetic acid, citric acid, and tartaric acid.

For alkalifying the solution, it is preferred to use sodium carbonate, sodium hydrogen carbonate, ammonium carbonate, or the like. Such carbonates are oxidized to percarbonic acid by electrolysis.

A surfactant may be added to the solution in order to further improve bactericidal activity. Addition of a surfactant to the solution not only improves the ability of the solution after electrolysis to wet the substance to be treated therewith through ejection, but also improves the affinity of the solution for the cell membranes of mold and germs. Thus, the bactericidal effect further improves.

Usable examples of the surfactant include anionic surfactants such as alkylbenzenesulfonic acid salts and polyoxyethylene alkyl ether sulfuric acid salts, cationic surfactants such as benzalkonium chlorides, amphoteric surfactants such as amine oxides (e.g., alkyldimethylamine oxides), and nonionic surfactants such as polyglycerol fatty acid esters and alkylglycosides. The concentration of the surfactant in the solution is preferably 0.01-10% by weight.

Besides those ingredients, an alcohol may be added to the solution for the purpose of, e.g., improving bactericidal activity and refreshing feeling. Furthermore, additives such as, e.g., a perfume, colorant, bactericide other than surfactants, thickener, enzyme, bleaching agent, chelating agent, electrolyte other than chlorine compounds, builder, antiseptic, and rust preventive may be added according to need. It is especially preferred from the standpoint of storage stability that the water to be electrolyzed should contain an antiseptic.

Head Having Trigger Spray Function

Figure 1:
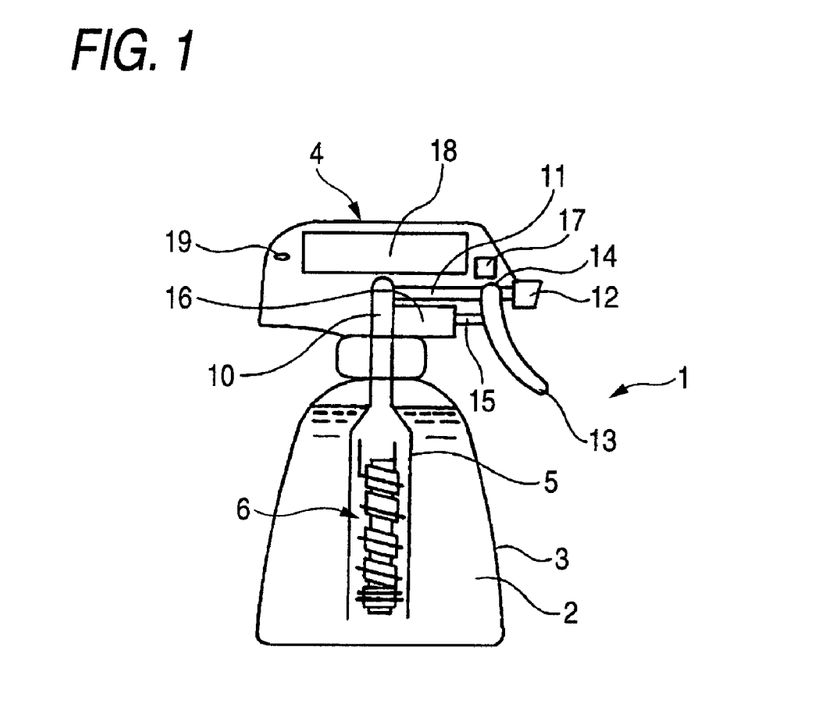
FIG. 1 is a diagrammatic vertical sectional view illustrating a first embodiment of the electrolytic water sprayer of the invention.
Figure 3:
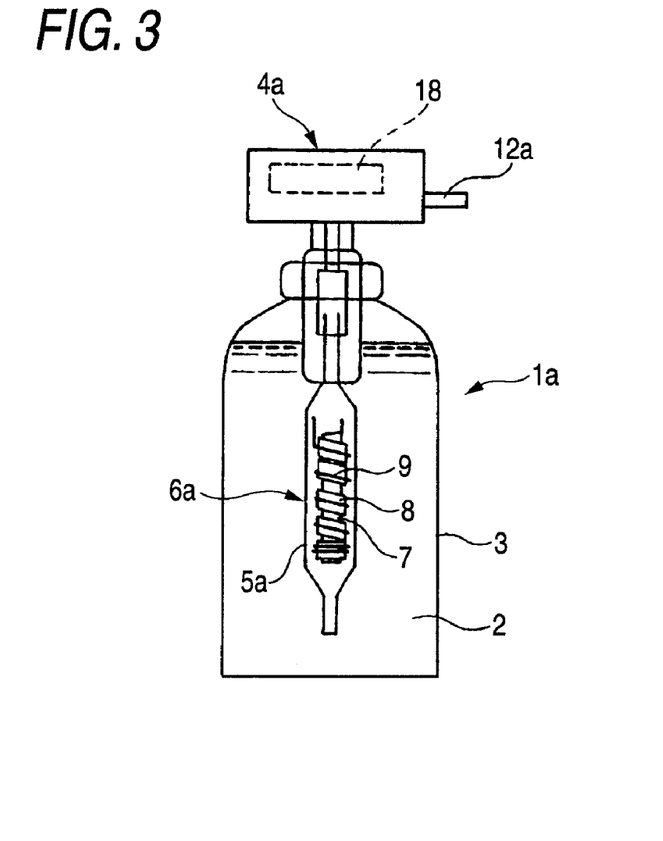
FIG. 3 is a diagrammatic vertical sectional view illustrating another embodiment of the electrolytic water sprayer of the invention.

As shown in FIGS. 1 and 3, a trigger spray has been fixed to a head in which a battery can be housed. The apparatus may be equipped with a device which generates power for electrolysis upon trigger operation, without employing a battery as a power source. In the case of battery driving, the battery may be a secondary battery, which is rechargeable. It is also possible to operate the apparatus with an adapter capable of supplying DC power from an AC power source.

The values of the voltage and current to be applied are suitably determined according to the concentration suitable for obtaining given bactericidal activity suitable for the substance to be sprayed and for the purpose of deodorization, sterilization, etc., and to the volume of the solution to be electrolyzed. One trigger operation preferably results in the ejection of 0.1-1 cc, and a voltage of about 3-25 V is applied between the electrodes. A device for changing the voltage to be applied to the electrodes may be disposed in the circuit.

With respect to electrolysis conditions, the temperature and the current density preferably are 5-40° C. and 0.01-1 $A/cm^2$, respectively, from the standpoints of the stability and activity of the peroxide yielded.

A switch for initiating/terminating voltage application to the electrodes has been preferably disposed in the trigger spray so that a voltage is preferably applied only when the apparatus is in use, i.e., pulling the trigger automatically results in switching on and returning the trigger results in switching off.

The sprayer of the invention may have a device which generates power for electrolysis upon ejection operation. Examples of this device include a motor which interlocks with the trigger. This motor is usually disposed in the trigger spray.

The ejecting apparatus of the invention can have means for indicating that electrolysis is being conducted. Examples of the means include an LED lamp which is made on during voltage application by a trigger operation. A function may be added which switches off the LED lamp when a specified current does not flow due to, e.g., battery exhaustion.

An embodiment of the electrolytic water production/ejecting apparatus of the invention works by the following mechanism. The apparatus is switched on by a trigger operation to cause a current to flow through the circuit. As a result, the current flows through the electrodes. In this operation, the raw water present in the tube is electrolyzed almost instantaneously and ejected or sprayed outward through the nozzle of the head by a piston/cylinder mechanism. Namely, in this sprayer of the invention, electrolysis is conducted simultaneously with the spraying operation (e.g., trigger operation). It is preferred that electrolytic water yielded by electrolysis should begin to be ejected within 1 second after the initiation of the trigger operation.

Besides the embodiment shown in the figures, there are various embodiments of the electrolytic water production/ejecting apparatus of the invention equipped with a trigger spray as a sprayer. Furthermore, there are trigger sprays having various mechanisms. The trigger sprays differ in the liquid passage therein, the position of the fulcrum of the trigger, etc. according to the mechanisms. However, any desired trigger spray can be employed in the sprayer of the invention.

Next, the electrolytic water ejecting apparatus (electrolytic water sprayer) of an embodiment of the invention is explained with respect to the embodiments shown in the figures.

FIG. 1 is a diagrammatic vertical sectional view illustrating a first embodiment of the electrolytic water sprayer of the invention.

The electrolytic water sprayer 1 shown in FIG. 1 comprises a vessel 3 for containing raw water 2 and a head 4 connected to the upper opening of this vessel 3. The material of the vessel 3 may be a rigid one or a flexible one. It is, however, preferred that the vessel 3 be made of a rigid material such as any of various rigid resins, metals, glasses, and ceramics. The capacity of the vessel 3 is preferably about 10-1,000 mL, more preferably 200-500 mL. The raw water 2 may be pure water or may be one containing one or more electrolytes dissolved therein, such as, e.g., sodium chloride, potassium chloride, and magnesium chloride.

In the vessel 3 has been disposed a suction tube 5. The lower end of the tube 5 is located in and open to the raw water 2, while the upper end thereof has a reduced diameter and extends into the head 4. Although the tube 5 in the embodiment shown in the figure has a reduced-diameter part, this reduced-diameter part is not always necessary and the tube may be a tube having an even diameter.

Figure 2:
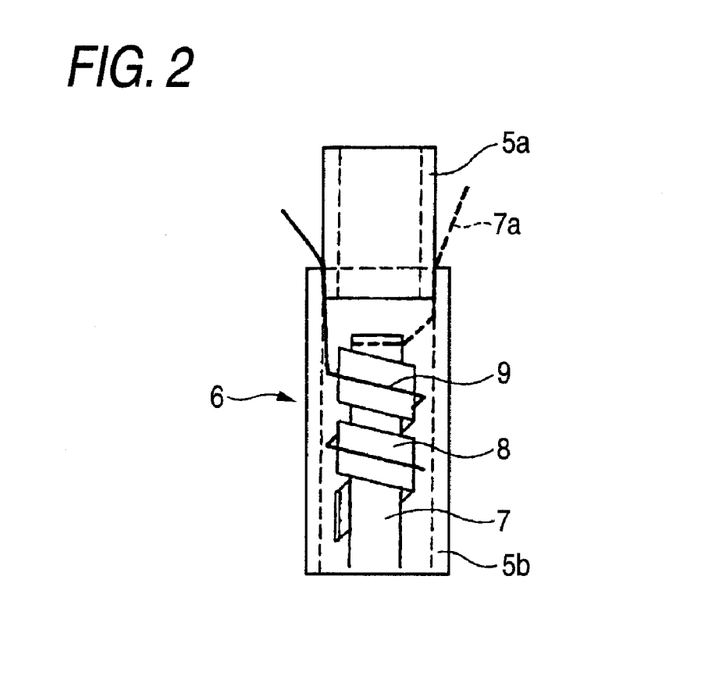
FIG. 2 is an enlarged view illustrating part of a membrane-electrode assembly embodiment different from the membrane-electrode assembly shown in FIG. 1.

An electrolytic unit 6 comprising an anode (rod electrode), a cathode (counter electrode), and a diaphragm has been housed in the suction tube 5. As shown in FIG. 2, this electrolysis unit 6 may, for example, comprise: an anode 7 which is a metallic rod electrode on which a catalyst has been deposited; a diaphragm 8 which is a strip-form ion-exchange membrane wound around the anode 7; and a cathode 9 comprising a metal wire wound around the diaphragm 8.

The reduced-diameter upper part of the suction tube 5 functions as a vertical channel 10, and the upper end thereof is connected to a horizontal channel 11 in the head 4.

At the other end of the horizontal channel 11 has been disposed a spray nozzle 12. A fulcrum 14 of a trigger arm 13 has been disposed on the slightly inner side of the spray nozzle 12 so that the trigger arm 13 is swingably movable around the fulcrum 14. The trigger arm 13 has been connected to a piston rod 15 extending inward so that the piston rod 15 travels in a cylinder 16 according to the movement of the trigger arm 13.

Numeral 17 denotes a trigger-engaged switch disposed so as to be in contact with the trigger arm 13; 18 denotes a power source battery disposed in the head 4; and 19 denotes an LED which is on only when electrolysis is proceeding.

The electrolytic water sprayer 1 having such constitution is held in a hand and an inward force is applied to the trigger arm 13 with the forefinger and middle finger. As a result, the trigger arm 13 swingably moves around the fulcrum 14, whereby the trigger-engaged switch 17 becomes on and a voltage is applied to the electrolytic unit 6. Simultaneously therewith, the piston in the cylinder 16 moves to lead the raw water 2 present in the vessel 3 to the electrolytic unit 6 in the suction tube 5, where this raw water 2 is electrolyzed to yield electrolytic water. The anode 7 in this electrolytic unit 6 has a catalyst, such as, e.g., a layer of conductive diamond, deposited on the surface thereof. Thus, electrolytic water containing ozone or other active species dissolved therein in a high concentration is obtained.

The electrolytic water yielded passes instantaneously through the vertical channel 10 and horizontal channel 11 and is sprayed through the spray nozzle 12 on a substance to be sterilized, together with air introduced through an outside-air intake opening not shown.

FIG. 2 is an enlarged view illustrating part of a membrane-electrode assembly embodiment different from the membrane-electrode assembly shown in FIG. 1. This embodiment is an improvement of the membrane-electrode assembly shown in FIG. 1. Like members as in FIG. 1 are designated by like numerals or signs and explanations thereon are omitted here.

In contrast to the embodiment shown in FIG. 1, which employed a single suction tube 5, the embodiment shown in FIG. 2 has a constitution in which a lower end part of a first suction tube 5a connected to the head has been fitted into a second suction tube 5b having an inner diameter equal to the outer diameter of the first suction tube 5a. The cathode 9 comprising a metal wire and a electric supply terminal 7a for the anode are led out through this fitted part.

FIG. 3 is a diagrammatic vertical sectional view illustrating still another embodiment of the electrolytic water sprayer of the invention. This embodiment is an improvement of the first embodiment shown in FIG. 1. Like members as in FIG. 1 are designated by like numerals or signs and explanations thereon are omitted here.

In the electrolytic water sprayer 1 as the first embodiment, electrolytic water was yielded and ejected from the nozzle 12 by applying an inward force to the trigger arm 13 with the forefinger and middle finger. In contrast, in the electrolytic water sprayer 1a according to this embodiment, a head 4a is pushed downward, whereby raw water 2 is electrolyzed with an electrolytic unit 6a in a suction tube 5a whose lower end has a reduced diameter. Thus, electrolytic water is yielded and sprayed through a nozzle 12a on a substance to be sterilized.

Figure 4:
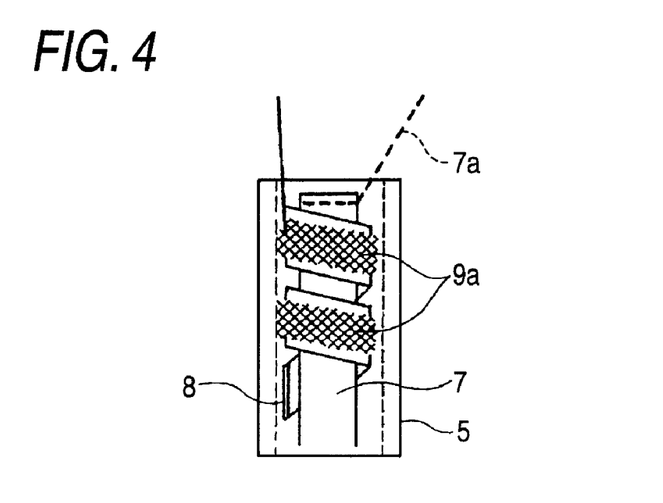
FIG. 4 is an enlarged view illustrating part of a membrane-electrode assembly embodiment different from the membrane-electrode assembly shown in FIG. 2.

The first and second embodiments shown above employ an electrolytic unit 6 in which a cathode 9 comprising a metal wire has been wound around a diaphragm 8, as shown in FIG. 2. However, the cathode may be constituted not by winding a metal wire but by bonding a foil 9a as shown in FIG. 4.

Figure 5:
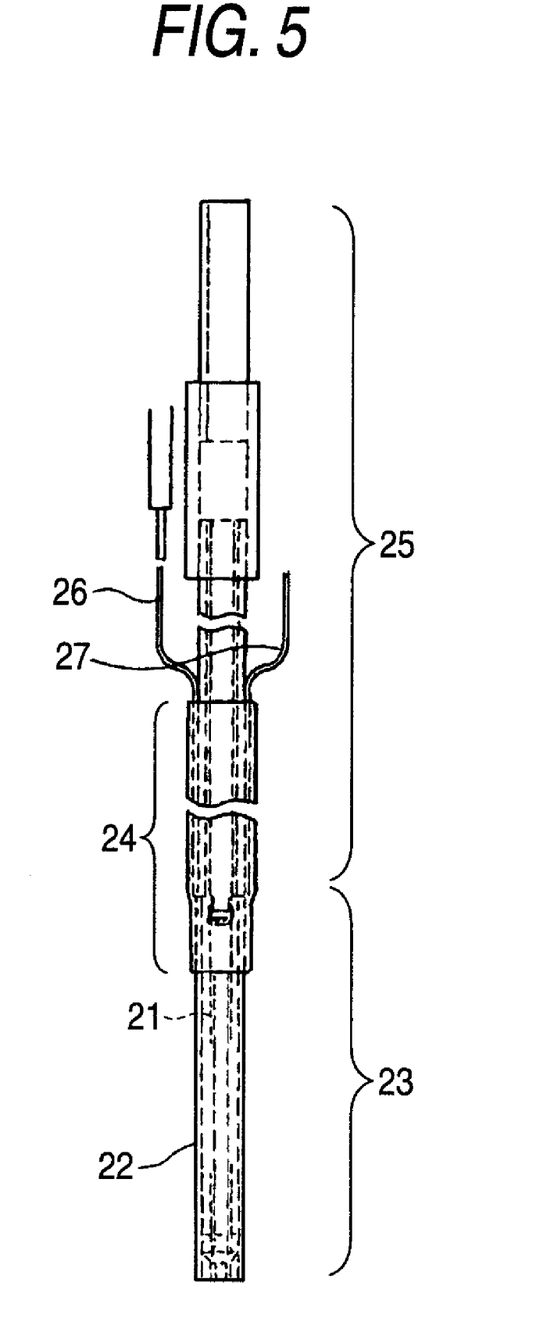
FIG. 5 is a view illustrating an electrolytic unit connected to a suction tube.

FIG. 5 is a view illustrating an electrolytic unit connected to a suction tube.

This figure shows an embodiment in which an electrolytic unit 23 comprising a first suction tube 22 and, housed therein, a membrane-electrode assembly 21 obtained by spirally covering the periphery of a rod electrode with a strip-form diaphragm and disposing a counter electrode on the surface of the diaphragm is connected to a second suction tube 25 with a shrink tube 24 for fixing.

The upper end of the electrolytic unit 23 is inserted into the lower end of the shrink tube 24 for fixing, and the second suction tube 25 is inserted into the shrink tube 24 so that the lower end of the second suction tube 25 is brought into contact with or near to the upper end of the electrolytic unit 23. Thereafter, the shrink tube 24 for fixing is thermally shrunk to connect the electrolytic unit 23 to the second suction tube 25. Numerals 26 and 27 denote copper wirings extending from a power source circuit. It is preferred that the copper wirings be disposed only in an upper part of the raw material vessel and be prevented, as much as possible, from coming into contact with the liquid.

Figure 6A:
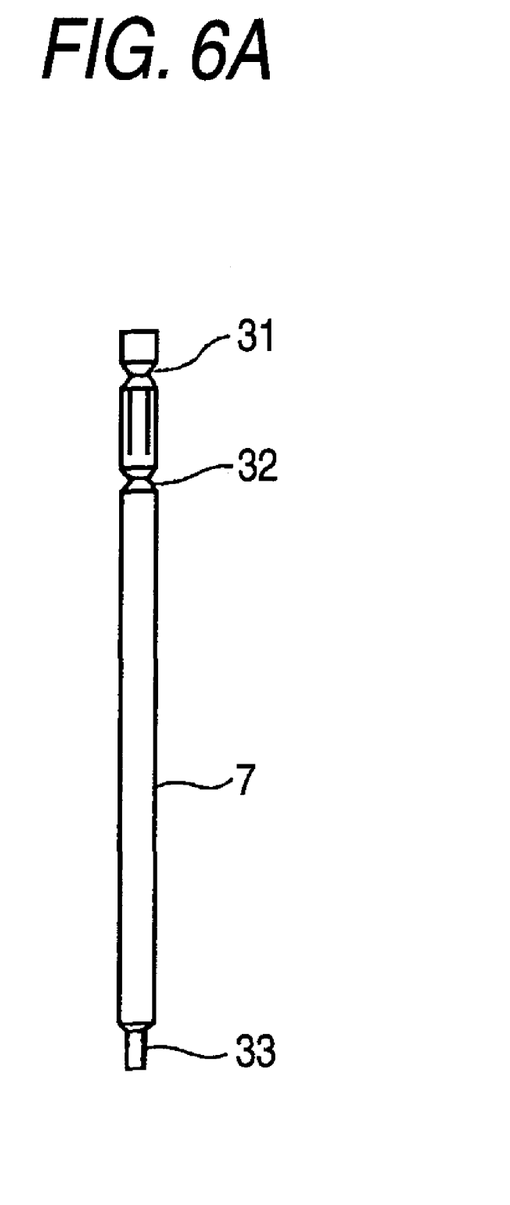
FIG. 6A and FIG. 6B are views respectively illustrating an example of the structure of a rod electrode and an example of the connection thereof to a feeder element.
Figure 6B:
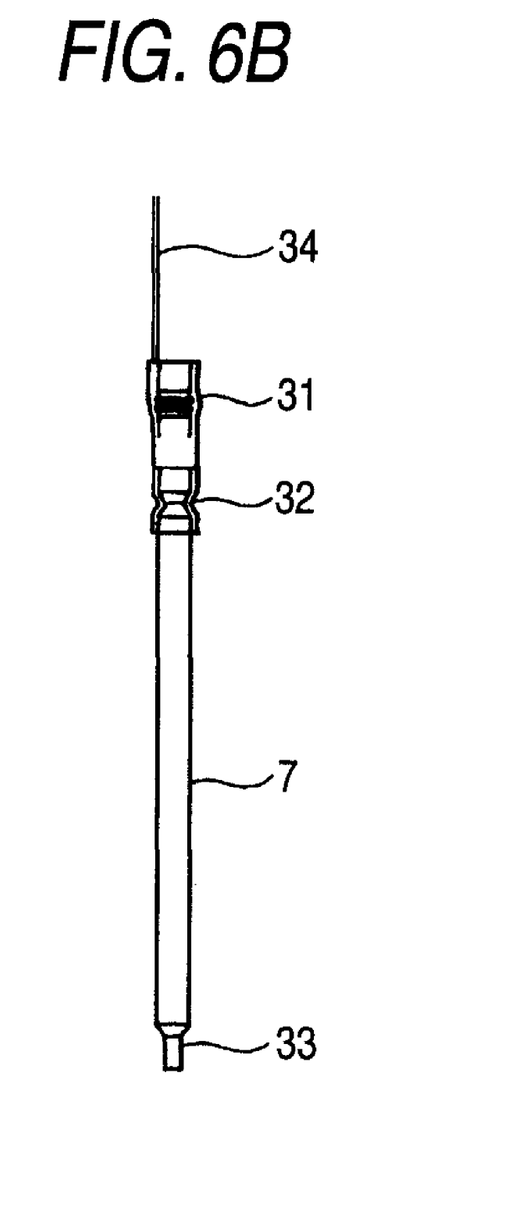

FIG. 6A and FIG. 6B are views respectively illustrating an example of the structure of a rod electrode and an example of the connection thereof to a feeder element.

As shown in FIG. 6A, the periphery of an upper end part of the rod electrode 7 has been cut to form a feeder-line fixing part 31. The periphery of that part of the rod electrode 7 which is located slightly below the feeder-line fixing part 31 has been cut to form a first diaphragm/wire electrode fixing part 32. Furthermore, the periphery of a lower end part of the rod electrode 7 has been cut to form a second diaphragm/wire electrode fixing part 33.

A feeder line 34 is connected and fixed to the feeder-line fixing part 31 as shown in FIG. 6B. Furthermore, a winding initiation part and winding termination part of a wire electrode wound through a diaphragm are fixed to the first diaphragm/wire electrode fixing part 32 and second diaphragm/wire electrode fixing part 33, respectively, although not shown in the figure.

The winding of a wire electrode and a diaphragm can be smoothly initiated by engaging an end part of the wire electrode with the first or second diaphragm/wire electrode fixing part 32 or 33. Besides this method, use may be made of a method in which that end part of a wire electrode which has been engaged with the first or second diaphragm/wire electrode fixing part 32 or 33 is fixed with a heat-shrinkable tube.

Furthermore, a method may be used in which the winding initiation part of a wire electrode is looped in an appropriate manner and this loop is fastened to a diaphragm or the rod electrode.

Figure 7:
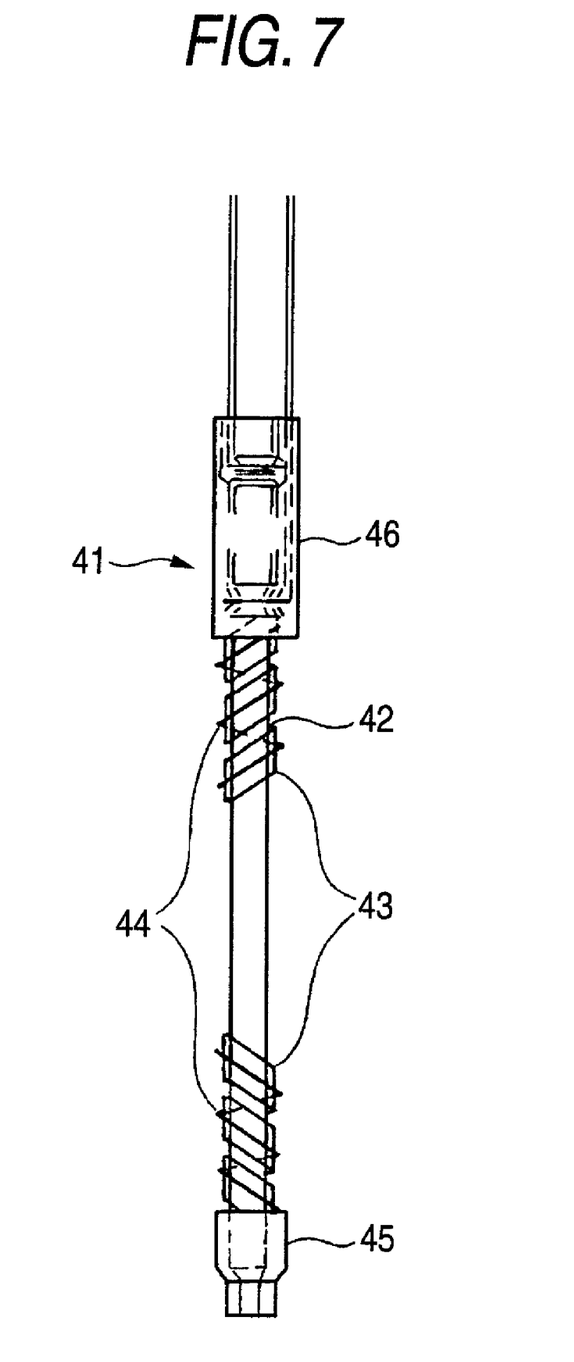
FIG. 7 is a view illustrating a membrane-electrode assembly different from the membrane-electrode assemblies shown in FIGS. 2 and 4.

FIG. 7 illustrates a membrane-electrode assembly different from the membrane-electrode assemblies shown in FIGS. 2 and 4.

The membrane-electrode assembly 41 shown in FIG. 7 comprises: an anode 42 which is a metallic rod electrode on which a catalyst has been deposited; a diaphragm 43 which is a strip-form ion-exchange membrane wound around the anode 42; and a cathode 44 comprising a metal wire wound around the diaphragm 43.

The embodiment shown in FIG. 7 has a first fixing tube 45 and a second fixing tube 46 which have been disposed respectively on a lower part and an upper part of the anode 42.

Figure 8:
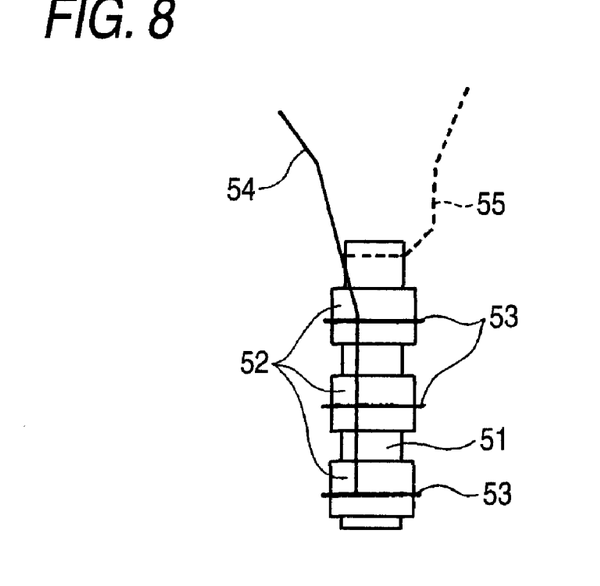
FIG. 8 is a diagrammatic view illustrating still a further embodiment of the membrane-electrode assembly.

FIG. 8 is a diagrammatic view illustrating a membrane-electrode assembly embodiment different from the membrane-electrode assemblies shown in FIGS. 2 and 4.

This embodiment comprises a rod anode 51, three ring-form strip diaphragms 52 which are disposed at regulator intervals and with which the periphery of the anode 51 is covered, and three wire cathodes 53 respectively wound around the diaphragms 52. These three cathodes 53 have been connected to one another with a conductor wire 54, and a electric supply terminal 55 has been connected to the rod anode 51.

EXAMPLES

The present invention is now illustrated in greater detail with reference to Examples and Comparative Examples, but it should be understood that the present invention is not to be construed as being limited thereto.

Example 1

A rod made of niobium (diameter, 2 mm; length, 5 cm) on which a conductive-diamond catalyst (dopant boron concentration, 500 ppm) had been deposited was used as an anode. A strip of an ion-exchange membrane (Nafion 350, manufactured by DuPont; thickness, 0.35 mm; width, 2 mm) was spirally wound as a diaphragm around the anode. A commercial platinum wire (diameter, 0.4 mm) was wound as a cathode on the diaphragm to obtain an anode-membrane-cathode assembly. An electrolytic unit including this membrane-electrode assembly fixed therein was connected in a trigger type sprayer shown in FIG. 1 to a PE resin tube attached to the intake. A 9V prismatic battery was mounted in the head of the trigger type sprayer. In a circuit part, the electrode terminals were connected to a variable resistor and a switch with a wiring. The vessel was filled with 500 cc of pure water.

The trigger was pulled, upon which the circuit was switched on and a current flowed between the battery and the cell. Simultaneously therewith, pure water was ejected. The amount of the water ejected was about 0.5 cc, and the quantity of electricity which flowed during this operation was 0.2 C (0.5 s×0.4 A). The terminal voltage of the cell was 9 V. The operation was repeatedly conducted 100 times. As a result, the ozone concentration in the solution ejected, which amounted to about 50 cc, was 5 ppm (corresponding to a current efficiency of 8%). The trigger operation was repeated 2,000 times, and the concentration of the ozone-containing water obtained thereafter was about 5 ppm.

In each of the Examples, the ozone concentration, hypochlorous acid concentration, persulfuric acid concentration, and percarbonic acid concentration were determined with an ultraviolet spectrophotometer and by iodometric titration with potassium iodide.

Example 2

The same test as in Example 1 was conducted, except that the vessel was filled with tap water containing 0.1 g/L sodium chloride. As a result, the ozone concentration and hypochlorous acid concentration in the solution yielded were 3 ppm and 0.5 ppm, respectively (corresponding to current efficiencies of 5% and 0.3%, respectively). The terminal voltage of the cell was 7.5 V and the current was 0.4 A. The trigger operation was repeated 2,000 times. As a result, the current efficiencies for these hydrolysis products were almost the same as the respective initial values. A deposit of calcium and magnesium compounds was observed in a small amount on the cathode.

Example 3

The same test as in Example 1 was conducted, except that a rod made of titanium on which an iridium oxide (5 g/m$^2$) catalyst had been deposited was used as an anode and tap water containing 0.1 g/L sodium chloride was used. As a result, the terminal voltage of the cell was 5.5 V and the current was 0.45 A. The hypochlorous acid concentration and ozone concentration in the solution yielded were 10 ppm and 0.1 ppm or lower, respectively.

Example 4

The same test as in Example 1 was conducted, except that a rod made of titanium on which a platinum catalyst (20 g/m$^2$) had been deposited was used as an anode. As a result, the terminal voltage of the cell was 6 V and the current was 0.4 A. The ozone concentration in the solution was 1 ppm. The trigger operation was repeated 2,000 times. As a result, the ozone concentration decreased to 0.5 ppm.

Example 5

The same test as in Example 2 was conducted, except that a rod made of titanium on which a platinum catalyst (20 g/m$^2$)

had been deposited was used as an anode and tap water containing 0.1 g/L sodium chloride was used. As a result, the terminal voltage of the cell was 5.5 V and the current was 0.45 A. The hypochlorous acid concentration and ozone concentration in the solution yielded were 3 ppm and 1 ppm, respectively.

Example 6

The same rod electrode as in Example 1 was used. Strips of an ion-exchange membrane (Nafion 350, manufactured by DuPont; thickness, 0.35 mm; width, 2 mm) each were formed into a ring beforehand and put as diaphragms on the anode. Commercial silver wires (diameter, 0.4 mm) were successively wound as cathodes around the diaphragm rings respectively to produce an anode-membrane-cathode assembly such as that shown in FIG. 8. An electrolytic unit including this membrane-electrode assembly fixed therein was evaluated in the same manner as in Example 1. As a result, the ozone concentration in the solution which was ejected by 100-time repetitions of the operation and amounted to about 50 cc was 4 ppm (corresponding to a current efficiency of 6%).

Reference Example 1

Figure 9:
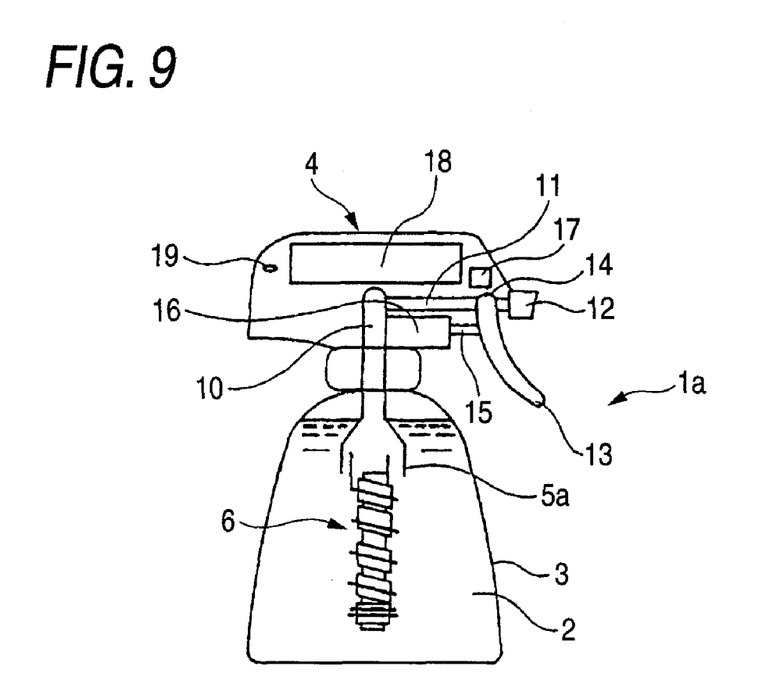
FIG. 9 is a diagrammatic vertical sectional view illustrating the electrolytic water sprayer used in Reference Example 1.

The electrolytic water sprayer shown in FIG. 9 was used. This electrolytic water sprayer 1a differs from the electrolytic water sprayer shown in FIG. 1 in that the suction tube 5a is shorter than the suction tube in FIG. 1 and that the electrolytic unit 6 has been disposed apart from the tube serving as a liquid channel in the sprayer. This sprayer was evaluated in the same manner as in Example 1. As a result, the ozone concentration in the solution which was ejected by 100 times repetitions of the operation and amounted to about 50 cc was 0.3 ppm.

While the present invention has been described in detail and with reference to specific embodiments thereof, it will be apparent to one skilled in the art that various changes and modifications can be made therein without departing from the spirit and scope thereof.

The present application is based on Japanese Patent Application No. 2006-254874 filed on Sep. 20, 2006, and the contents thereof are incorporated herein by reference.

What is claimed is:

1. A membrane-electrode assembly comprising:
a first electrode having a shape of a rod-form or a cylindrical-form;
a strip-form diaphragm covering the periphery of the first electrode; and
a second electrode disposed on a surface of the strip-form diaphragm,
wherein the strip-form diaphragm spirally covers the periphery of the first electrode.

2. The membrane-electrode assembly of claim 1, wherein the strip-form diaphragm covers the periphery of the first electrode so as to form a space between parts of the diaphragm.

3. The membrane-electrode assembly of claim 1, wherein the strip-form diaphragm includes recesses and protrusions.

4. The membrane-electrode assembly of claim 1, wherein at least one of the first electrode and the second electrode includes openings formed therethrough.

5. The membrane-electrode assembly of claim 1, wherein the strip-form diaphragm comprises an ion-exchange membrane.

6. The membrane-electrode of claim 1, wherein the second electrode spirally covers a periphery of the strip-form diaphragm.

7. An electrolytic unit comprising:
a membrane-electrode assembly comprising:
a first electrode having a shape of a rod-form or a cylindrical-form;
a strip-form diaphragm covering the periphery of the first electrode; and
a second electrode disposed on a surface of the strip-form diaphragm,
wherein the strip-form diaphragm spirally covers the periphery of the first electrode;
a tube, the membrane-electrode assembly being fixed in the tube; and
an electric supply terminal connected to at least one of the first electrode and the second electrode in the tube.

8. An electrolytic water ejecting apparatus comprising:
a vessel containing a raw water;
the electrolytic unit according to claim 7;
a head to eject an electrolytic water prepared by electrolyzing the raw water with the electrolytic unit.

9. A method of sterilization with an electrolytic water, the method comprising:
electrolyzing a raw water with a membrane-electrode assembly comprising:
a first electrode having a shape of a rod-form or a cylindrical-form;
a strip-form diaphragm covering the periphery of the first electrode; and
a second electrode disposed on a surface of the strip-form diaphragm to produce a electrolytic water; and
ejecting the electrolytic water to a substance to be sterilized.

* * * * *